United States Patent [19]

Siemer et al.

[11] 4,312,665

[45] * Jan. 26, 1982

[54] RIPENING OF GRAPES

[75] Inventors: Sidney R. Siemer, Fresno, Calif.;
Richard S. Gordon, St. Louis, Mo.;
Louis G. Nickell, Chicago, Ill.

[73] Assignee: W. R. Grace & Co., Columbia, Md.

[ * ] Notice: The portion of the term of this patent subsequent to Apr. 11, 1997, has been disclaimed.

[21] Appl. No.: 157,572

[22] Filed: Jun. 9, 1980

Related U.S. Application Data

[63] Continuation-in-part of Ser. No. 33,884, Apr. 27, 1979, Pat. No. 4,231,788.

[51] Int. Cl.$^3$ ............................................. A01N 37/02
[52] U.S. Cl. ..................................................... 71/113
[58] Field of Search ........................................... 71/113

[56] References Cited

U.S. PATENT DOCUMENTS

| | | | |
|---|---|---|---|
| 3,870,503 | 3/1975 | Nickell | 71/113 X |
| 3,994,715 | 1/1976 | Nickell | 71/122 |
| 4,033,755 | 7/1977 | Nickell | 71/113 |

OTHER PUBLICATIONS

Jung et al., Chem. Abst. vol. 67, (1967), 89968a.

*Primary Examiner*—Catherine L. Mills
*Attorney, Agent, or Firm*—P. M. Pippenger

[57] ABSTRACT

Disclosed herein is a method of increasing the sugar (primarily glucose and fructose) content in grapes by applying to grape vines (primarily to the leaves) a compound which is vanillin or a carboxylic acid salt having from 3 to 5 carbon atoms. Grapes are customarily harvested when the sugar level is about 16% "Brix", and application of the compounds of the present invention gives the grower a better means of controlling sugar level so that the fruit can be harvested in an orderly manner.

8 Claims, No Drawings

RIPENING OF GRAPES

REFERENCE TO RELATED APPLICATION

The present application is a continuation-in-part of U.S. Ser. No. 33,884 (now U.S. Pat. No. 4,231,788) by Sidney R. Siemer, Richard S. Gordon and Louis G. Nickell, filed Apr. 27, 1979 and entitled "Ripening of Grapes".

BACKGROUND OF THE INVENTION

Grapes are customarily harvested at a sugar level of about 16 percent Brix. This value can be determined by randomly selecting one or more berries from a bunch of grapes to be marketed, squeezing out the juice, filtering if necessary to remove solids, and "reading" the juice with a hand refractometer to determine the % Brix. This method is described generally in the publication by the California Department of Food and Agriculture entitled "Fruit and Vegetable Standardization," Title III, Article 25, sec. 1436.5 (Register 75, No. 4, 1-25-75). For purposes of the present application an additional method has been employed to determine the sugar level. This method (designated as the "Sugar Content") involves selecting the second bunch on each cane (most vines have four canes), selecting the second shoulder in the bunch, removing all grapes, admixing and extracting the juice from all of these berries followed by reading the % Brix as above. The values from the four canes are then averaged to give the "Sugar Content" for the grapes on a particular vine. Another parameter measured for purposes of the present invention is the acid level of the grapes. This value is determined by titrating the juice used in determining Sugar Content against NaOH. This method is described in the California Department of Food and Agriculture publication described above, Article 25, section 1436.7 entitled "Grapes, Titration to Determine Soluble Solids to Acid Ratio." The sugar/acid ratio used in the Example is determined by dividing the Sugar Content by the acid value.

In California and other areas, it is customary to harvest grapes when the % Brix reaches 16 percent. In many situations it is desirable to hasten the increase in sugar level to the desired 16 percent level or higher (for wine grapes, raisins) so that the orderly harvest, processing and marketing of the grapes (or products therefrom) can be maintained. Accordingly, a major objective of the present invention is to enable grapes to be harvested "on schedule".

The use of ammonium isobutyrate (AIB) as a ripening agent for sugarcane is described in U.S. Pat. No. 4,033,755. Other relevant U.S. Pat. Nos. included 3,870,503 (sodium isobutyrate), 3,909,238 (polyethoxylated surfactants), and 3,994,715 (vanillin).

DESCRIPTION OF THE INVENTION

The invention is a method for increasing the percent Brix in grapes prior to harvest by applying to the leaves of the vine a compound selected from the group consisting of vanillin or a carboxylic acid salt containing 3 to 5 carbon atoms. The carboxylic acid salt should be water soluble or at least water dispersible through the use of a surfactant. Suitable salts include AIB, calcium isobutyrate, magnesium isobutyrate, sodium isobutyrate, potassium isobutyrate, ammonium butyrate, sodium butyrate, ammonium propionate, sodium propionate, calcium propionate, magnesium propionate and potassium propionate. Generally, the acid cation is sodium, potassium, calcium, magnesium or ammonium.

In practicing the invention it is important to realize that the Sugar Content tends to fluctuate from season to season and from vine to vine. Therefore, application of the compounds of the invention will not always result in the same increase in sugar level in the same amount of time. For example, superior seedless grapes were treated at 10 and 20 lbs/acre of ammonium isobutyrate but showed little response at either level. However there was a large variation in the maturity levels of the grapes at the time of treatment, making it difficult to accurately measure the response.

Generally, the compounds should be applied at from 4 to 40 days prior to the intended harvest time. In some vines it may be possible to increase the sugar level (i.e., % Brix) to 16 percent by application as little as 4 days prior to harvest, whereas in the majority of cases, application at from 7 to 28 days prior to harvest is preferable, i.e., the sugar level is most likely to be 16 percent or more at the time it is desired to harvest the fruit.

The compounds are applied at a rate of from 1 to 50 pounds per acre and 2 to 10 pounds is optimal. Above 10 pounds per acre the increase in effect is nominal, especially in view of the increased cost of the compound applied. It is also necessary to employ a surfactant (exemplified below) where the ripening agent is the salt of a volatile organic acid having 3-5 carbon atoms, e.g., ammonium isobutyrate. Use of the surfactant causes a significant increase in ripening activity as opposed to the use of the salt without an adjuvant. On a weight basis the ratio of the acid salt to the surfactant can be from 10 to 1 although 2-6 is preferred and 2-4 is most preferable. It has also been found that the acid salts (e.g., ammonium isobutyrate) cause damage to the berries when sprayed to "run-off". The damage is believed to arise because the formulation accumulates in droplet form on the lower portion of the berry, providing extended exposure to relatively large amounts of the ripening agent. This problem can of course be minimized by not spraying to run-off or by applying reduced levels of the ripening agent, i.e., from 1 to 10 pounds of ripening agent per acre, exclusive of the surfactant, water and any other materials in the formulation.

The compounds are employed in the form of aqueous solutions or dispersions. Generally, where the application device is a spray gun, boom or other device where the solution is expressed through a narrow orifice by pressure, the application rate is 50 to 200 gallons of solution per acre. Where the application is by means of an air sprayer (e.g., a "speed Sprayer"), i.e., the solution is entrained in a fast moving air stream, more concentrated solutions are employed and about 5 to 50 gallons per acre can be used. Regardless of the amount of solution employed, the pounds of active ingredients per acre should be within the ranges described above.

In the aqueous solutions employed the surfactant level is generally from 0.1 to 15 percent by volume of the total formulation and 0.1 to 1½ percent is preferred. Suitable surfactants which can be employed include:
 sorbitan monolaurate—undiluted
 sorbitan monopalmitate—50% in $H_2O$
 sorbitan monostearate—30% in $H_2O$
 sorbitan monooleate—undiluted
 sorbitan trioleate—undiluted
 polyoxyethylene (20) sorbitan monolaurate—undiluted polyoxyethylene (4) sorbitan monolaurate—undiluted
polyoxyethylene (20) sorbitan monopalmitate—undiluted
polyoxyethylene (20) sorbitan monostearate—undiluted
polyoxyethylene (4) sorbitan monostearate—60% in H$_2$O
polyoxyethylene (20) sorbitan tristearate—60% in H$_2$O
polyoxyethylene (20) sorbitan monooleate—undiluted
polyoxyethylene (5) sorbitan monooleate—undiluted
polyoxyethylene (20) sorbitan trioleate—undiluted
polyoxyethylene (2) cetyl ether 98 at 60% in H$_2$O, 100 at 20% in H$_2$O
polyoxyethylene (10) cetyl ether—60% in H$_2$O
polyoxyethylene (20) cetyl ether—60% in H$_2$O
polyoxyethylene (2) stearyl ether—60% in H$_2$O
polyoxyethylene (10) stearyl ether—60% in H$_2$O
polyoxyethylene (20) stearyl ether—60% in H$_2$O
polyoxyethylene (2) oleyl ether—undiluted
polyoxyethylene (10) oleyl ether—undiluted
polyoxyethylene (20) oleyl ether—undiluted The above materials are commonly available under trade names such as "Tween", "Span", "Brij" and "Carbowax". Other surfactants which reduce surface tension can also be employed.

The term "grape" as used herein means *Vitis vinifera* generally and includes, for example, Thompson Seedless, Perlettes, Rebeir, Seedless Tokay, Interlocken Series and related hybrids.

EXAMPLE

AIB was applied to grape vines (Thompson Seedless) at the rate of 2.5 and 50 pounds of compound per acre. In applying the compounds, solutions were prepared by dispersing the required amount of the compound in water. For an application level of 2.5 pounds/acre, 2.5 pounds of compound is used for every 200 gallons of water. Fifty pounds is used for an application rate of 50 pounds/acre. Tween 20 (polyoxyethylene (20) sorbitan monolaurate) was employed as the surfactant. The AIB/surfactant weight ratio was 2:1.

In California where the tests of this example were performed, the average number of grape vines per acre is about 500. Therefore, the average amount of solution applied to each vine is about 0.4 gallons. The solutions were applied using a CO$_2$ hand sprayer. The rate of application, time prior to harvest, and results obtained are set forth in the following Table.

TABLE

A

|  | 0 (Control) (8 vines) | 2.5 lbs/Acre (4 vines) | 50 lbs/Acre (4 vines) |
|---|---|---|---|
| Sugar Content | 16.4% | 17.2% | 17.8% |
| # of Bunches at 16% Brix of higher | 66.8% | 83.0% | 92.4% |
| Sugar/Acid Ratio | 28.3 | 29.9 | 29.9 |

B

|  | Control (zero lbs of active ingredient/acre) | | 2.5 lbs of active ingredient/acre | | 50 lbs of active ingredient/acre | |
|---|---|---|---|---|---|---|
|  | Sugar Content | Bunches At 16% Brix | Sugar Content | Bunches At 16% Brix | Sugar Content | Bunches At 16% Brix |
| Vine 1 | 15.720 | 3/10 | 18.118 | 11/11 | 18.015 | 12/13 |
| Vine 2 | 16.923 | 10/13 | 18.258 | 12/12 | 18.280 | 15/15 |
| Vine 3 | 16.693 | 11/15 | — | — | — | — |
| Vine 4 | 16.093 | 10/15 | — | — | — | — |
| Avg. | 16.357 | 34/53 | 18.188 | 23/23 | 18.148 | 27/28 |
| Increase (%) | — | — | 11.2% | 35.9% | 11.1% | 32.3% |

C

|  | 0 | 50 lbs. |
|---|---|---|
| Bunches | 24 | 26 |
| Bunches at 16% Brix | 6 | 16 |
| % Passing | 25% | 61.5% |
| Sugar Content | 14.86% | 15.99 |
| % Increase | — | 7.6% |

What is claimed is:

1. A method for increasing the % Brix in grapes prior to harvest by applying a compound selected from the group consisting of carboxylic acid salts containing from 3 to 5 carbon atoms in combination with a surfactant, wherein the acid salt/surfactant weight ratio is from 10 to 1.

2. A method as in claim 1 wherein a salt of propionic acid is employed.

3. A method as in claim 1 wherein a salt of butyric acid is employed.

4. A method as in claim 1 wherein a salt of isobutyric acid is employed.

5. A method as in claim 1 wherein the carboxylic acid salt is ammonium isobutyrate.

6. A method as in claim 1 wherein the compound is applied to increase the % Brix to 16% at the time of harvest.

7. A method as in claim 1 wherein the acid salt/surfactant weight ratio is 2 to 6.

8. A method as in claim 1 wherein the acid salt/surfactant weight ratio is 2 to 4.

* * * * *